US005941887A

United States Patent [19]

Steen et al.

[11] Patent Number: 5,941,887

[45] Date of Patent: Aug. 24, 1999

[54] SLEEVE FOR A SURGICAL INSTRUMENT

[75] Inventors: Mark E. Steen, Chino Hills; Gloria D. Sefton, Trabuco Canyon, both of Calif.

[73] Assignee: Bausch & Lomb Surgical, Inc., Claremont, Calif.

[21] Appl. No.: 08/706,803

[22] Filed: Sep. 3, 1996

[51] Int. Cl.[6] .......... A61F 9/00

[52] U.S. Cl. .......... 606/107; 606/169; 604/22

[58] Field of Search .......... 604/19, 22; 606/1, 606/107, 167, 169–171, 185

[56] References Cited

U.S. PATENT DOCUMENTS

| | | |
|---|---|---|
| 2,432,641 | 12/1947 | Wilson . |
| 3,589,363 | 6/1971 | Banko et al. . |
| 3,659,607 | 5/1972 | Banko . |
| 3,693,613 | 9/1972 | Kelman . |
| 3,805,787 | 4/1974 | Banko . |
| 3,882,872 | 5/1975 | Douvas et al. . |
| 3,902,495 | 9/1975 | Weiss et al. . |
| 3,945,375 | 3/1976 | Banko . |
| 3,948,273 | 4/1976 | Sanders . |
| 4,099,147 | 7/1978 | McAvoy . |
| 4,180,074 | 12/1979 | Murry et al. . |
| 4,223,676 | 9/1980 | Wuchinich et al. . |
| 4,316,161 | 2/1982 | Moore et al. . |
| 4,370,131 | 1/1983 | Banko . |
| 4,428,748 | 1/1984 | Peyman et al. . |
| 4,504,264 | 3/1985 | Kelman . |
| 4,515,583 | 5/1985 | Sorich . |
| 4,516,398 | 5/1985 | Wuchinich . |
| 4,573,979 | 3/1986 | Blake . |
| 4,578,059 | 3/1986 | Fabricant et al. . |
| 4,609,368 | 9/1986 | Dotson, Jr. . |
| 4,634,420 | 1/1987 | Spinosa et al. . |
| 4,643,717 | 2/1987 | Cook et al. . |
| 4,652,255 | 3/1987 | Martinez . |
| 4,655,743 | 4/1987 | Hyde . |
| 4,674,502 | 6/1987 | Imonti . |
| 4,681,561 | 7/1987 | Hood et al. . |

(List continued on next page.)

FOREIGN PATENT DOCUMENTS

| | | |
|---|---|---|
| 269870 | 10/1987 | European Pat. Off. . |
| 375302 | 12/1989 | European Pat. Off. . |
| 376562 | 12/1989 | European Pat. Off. . |

OTHER PUBLICATIONS

Trade Journal Advertisement for new phaco tip from Storz Ophthalmics, *Ophthalmology Times*, Jun. 1, 1996, p. 34.

Advertisement for The Cobra Seal, ASCRS '96, Jun. 1, 1996, p. 85.

"Scleral and Corneal Burns During Phacoemulsification with Viscoeelastic Materials," *ECRI*, 17(12):377–79 (Dec. 88).

Polack et al., "The Phacoemulsification Procedure, III, Corneal Complications," *Invest. Ophthal. Vicual Sci.* 39–46 (1977).

Strobel et al., "Phaco–Emulsification and Planned ECCE: Intraoperative Differences in Intraocular Heating," *Eur. J. Implant, Ref. Surg.* 3:135–38 (1991).

*Primary Examiner*—Glenn K. Dawson
*Attorney, Agent, or Firm*—Banner & Witcoff Ltd.; Steven P. Schad; Rita D. Vacca

[57] ABSTRACT

A surgical sleeve which includes a series of spaced apart rings on an interior wall surface encircling a slender cutting tip. The sleeve completely enshrouds the tip in an unstressed condition in order to avoid inadvertent injury to the interior portions of the eye. The sleeve, however, automatically retracts during use to expose the free end of the tip to effect emulsification of the natural lens. The spaced rings further reduce the surface contact between the sleeve and the tip and define a transverse channel through which fluid may flow when lateral pressure is applied to the sleeve. As a result, the sleeve is able to effectively remove heat from the tip even under adverse conditions and alleviate the risk of burning the corneal tissue.

30 Claims, 4 Drawing Sheets

36 24 21 28 16 10 40 26 45 38 39 18 20 22 46 34 23 17 19 14 12

U.S. PATENT DOCUMENTS 4,705,500 11/1987 Reimels et al. .
4,764,165 8/1988 Reimels et al. .
4,787,889 11/1988 Steppe et al. .
4,808,154 2/1989 Freeman .
4,816,017 3/1989 Hood et al. .
4,816,018 3/1989 Parisi .
4,869,715 9/1989 Sherburne .
4,897,079 1/1990 Zaleski et al. .
4,922,902 5/1990 Wuchinich et al. .
4,983,160 1/1991 Steppe et al. .
5,015,227 5/1991 Broadwin et al. .
5,038,756 8/1991 Kepley .
5,059,204 10/1991 Lawson et al. .
5,084,009 1/1992 Mackool .
5,123,903 6/1992 Quaid et al. .
5,151,083 9/1992 Pichler .
5,151,084 9/1992 Khek .
5,162,044 11/1992 Gahn et al. .
5,188,589 2/1993 Wypych .
5,199,943 4/1993 Wypych .
5,242,385 9/1993 Strukel .
5,282,786 2/1994 Ureche .
5,286,256 2/1994 Mackool .
5,346,502 9/1994 Estabrok et al. ........................ 606/169
5,354,265 10/1994 Mackool .
5,417,654 5/1995 Kelman .
5,464,389 11/1995 Stahl .
5,478,338 12/1995 Reynard .
5,486,162 1/1996 Brumbach .
5,496,342 3/1996 Urich .
5,505,693 4/1996 Mackool .

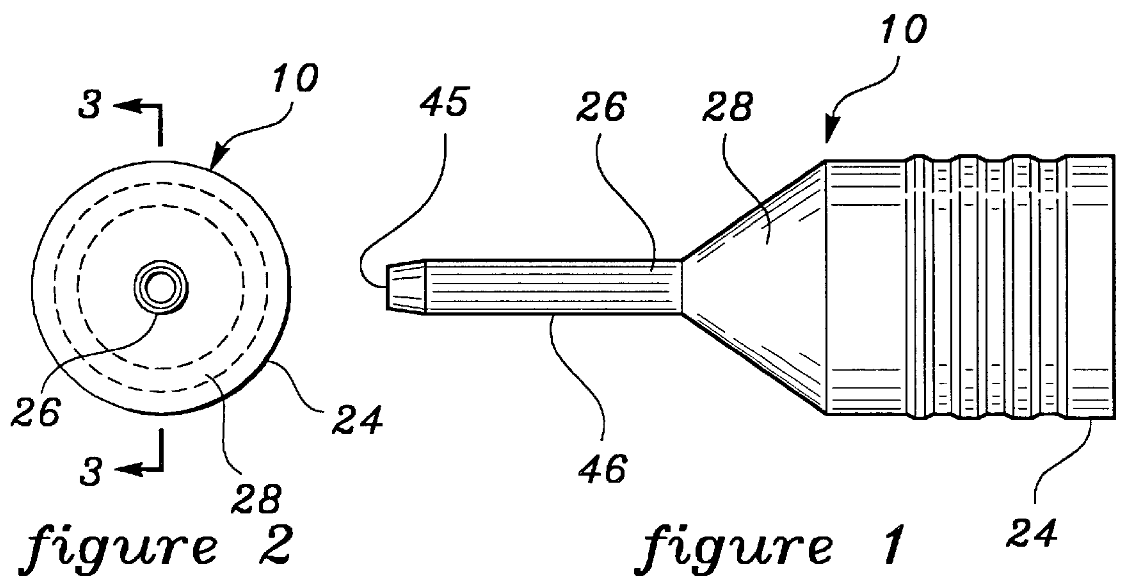
figure 2
figure 1
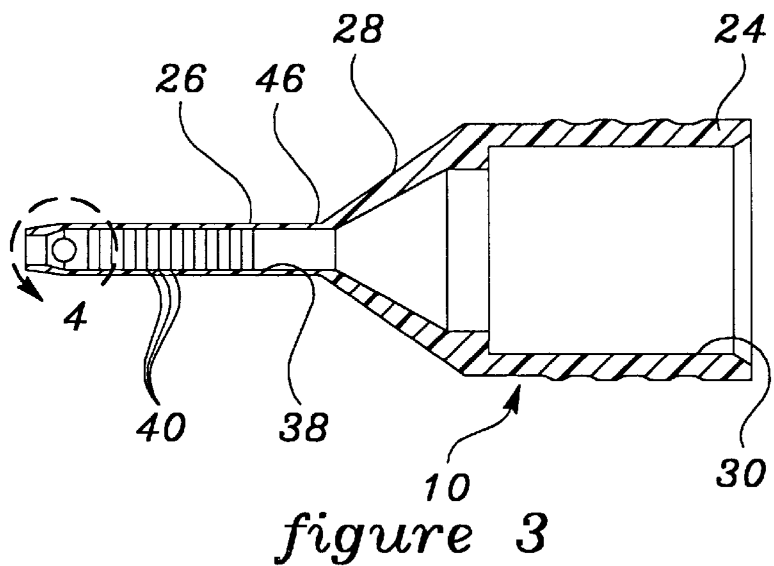
figure 3
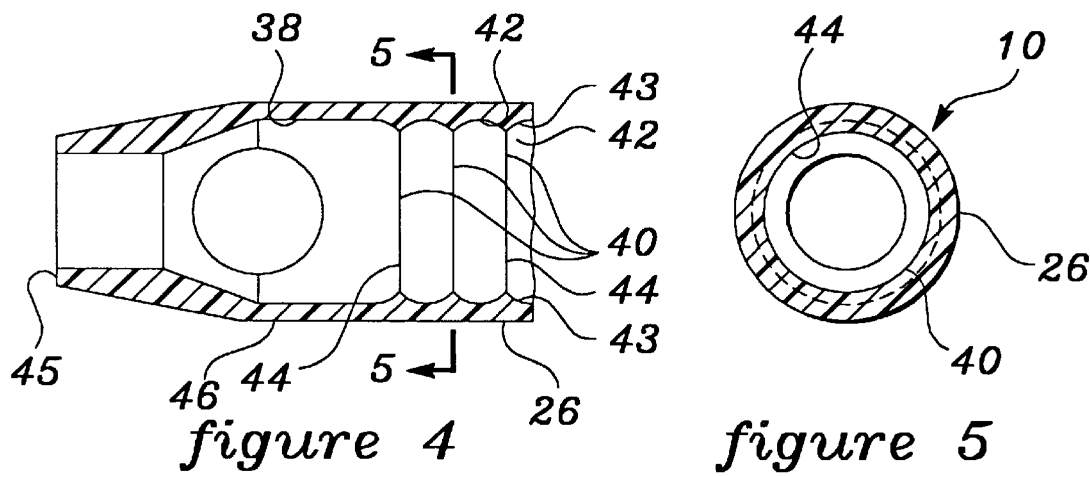
figure 4
figure 5

40
26
38
43

10
45
48
39
45
34
26
46
40
22
10
20
38
16
18
28
19
21
17
24

23
36
14
12

SLEEVE FOR A SURGICAL INSTRUMENT

FIELD OF THE INVENTION

The present invention pertains to a sleeve for attachment to a surgical instrument for removing the natural lens of an eye. The surgical sleeve surrounds a slender cutting tip of the instrument and defines a fluid conduit about the tip.

BACKGROUND OF THE INVENTION

The natural crystalline lens of the eye plays a primary role in focusing light onto the retina for proper vision. However, the natural lens at times is replaced with an artificial lens to make a refractive correction or because of damage or injury to the natural lens. Under these circumstances, the natural lens is surgically removed from the eye.

Surgical procedures which require only a small incision to be made in the eye have been developed for removing the natural lens. In accordance with these procedures, a slender cutting tip of a surgical instrument is inserted through the incision to emulsify the natural lens—typically through the use of ultrasonic vibrations. A sleeve surrounds the tip to shield the corneal tissue from the action of the tip, and define an annular conduit for the passage of a fluid which acts to cool the tip and irrigate the eye. The free end of the cutting tip, however, still projects beyond the sleeve to engage and emulsify the natural lens. Great care must therefore be taken by the surgeon to ensure that only the lens is engaged by the tip so that injury is avoided. The emulsified portions of the lens are aspirated from the eye through a central bore in the tip.

Further, during an operation, the surgical instrument is manipulated to remove the entire lens. On account of this movement, the sleeve can at times become pinched between the tip and the corneal tissue of the eye. The frictional contact between the sleeve and the vibrating tip can generate a significant amount of heat at the surgical site. The corneal tissue can be damaged by the heat in a matter of a few seconds.

SUMMARY OF THE INVENTION

The present invention pertains to a surgical sleeve which functions to protect the eye against injury during a procedure to remove the natural lens. The sleeve includes a cannula which encircles and extends beyond the slender cutting tip of a surgical instrument to enshroud the tip and protect the eye when the sleeve is in an unstressed condition. The cannula automatically retracts to expose the tip for emulsifying the natural lens when the tool is pressed axially against the lens. The cannula is provided with a series of transverse rings which are axially spaced from one another. The rings enable the cannula to be retracted and expanded.

The spaced rings also function to protect the eye from undue heat generated by the instrument. More specifically, the rings reduce the surface contact between the sleeve and the tip, and define transverse channels through which fluid may flow when lateral pressure is applied to the sleeve. As a result of the reduced contact and continual fluid flow, severe temperature increases are avoided to prevent burning of the corneal tissue.

BRIEF DESCRIPTION OF THE DRAWINGS

FIG. 1 is a side view of a surgical sleeve in accordance with the present invention.

FIG. 2 is a front end view of the sleeve.

FIG. 3 is a cross-sectional view taken along line 3—3 in FIG. 2.

FIG. 4 is a partial, enlarged sectional view of the end of the sleeve, identified by line 4 in FIG. 3, with the cannula in an expanded condition.

FIG. 5 is a cross-sectional view taken along line 5—5 in FIG. 1.

DETAILED DESCRIPTION OF THE PREFERRED EMBODIMENTS

Figures 6, 7:
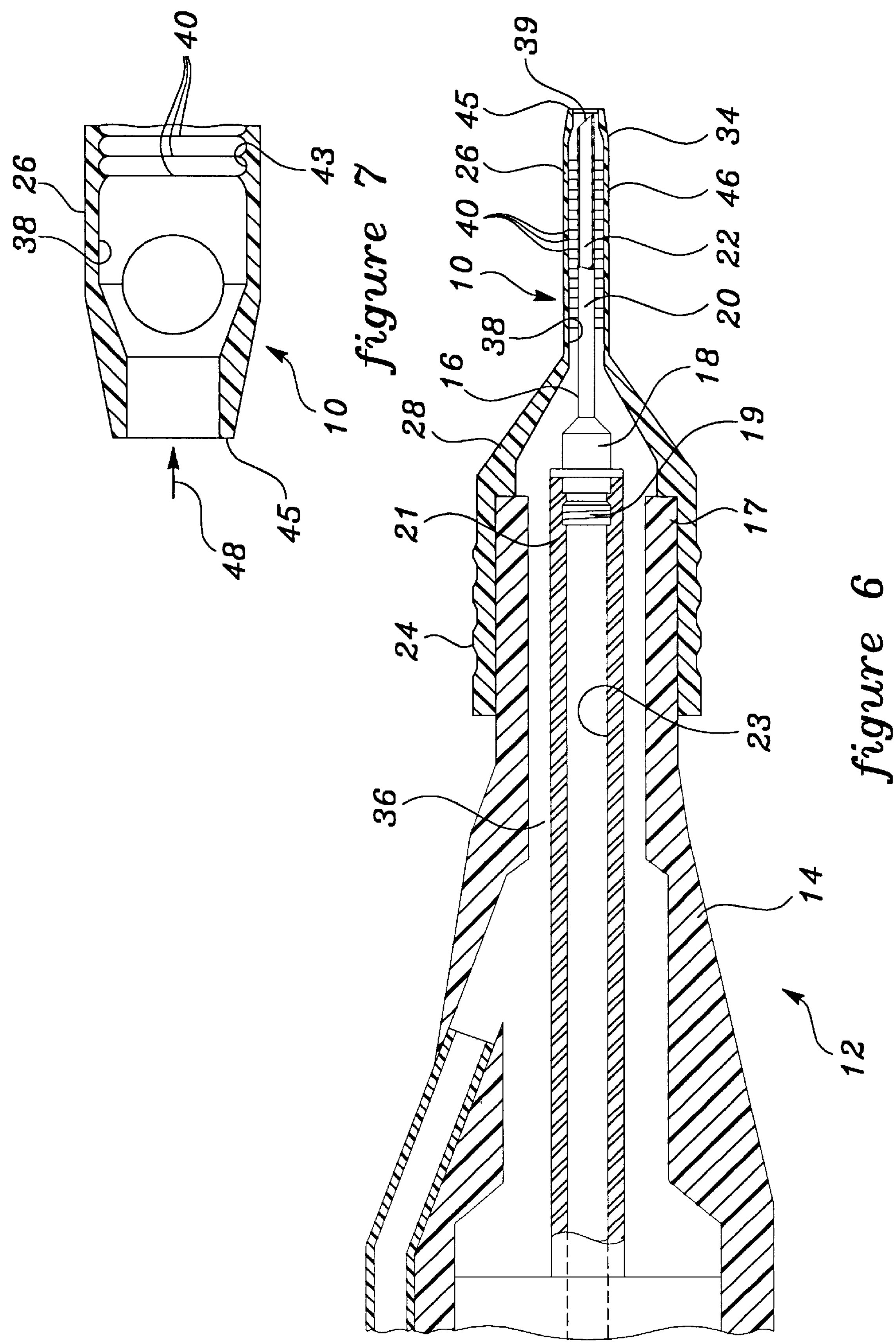
FIG. 6 is a sectional view of the sleeve mounted on a surgical instrument.
FIG. 7 is a partial, enlarged sectional view of the end of the sleeve in a retracted condition.

The present invention pertains to a sleeve 10 which attaches to a surgical instrument provided with a slender cutting tip for removing the natural lens of an eye (FIGS. 1–6). The tip is typically driven to vibrate ultrasonically in an axial direction (e.g., phacoemulsification) to emulsify the lens. As an example, surgical instrument 12 (FIG. 6) includes a casing 14 to be grasped and manipulated by a surgeon, and a slender cutting tip 16 which projects from a distal end 17 of the casing.

Tip 16 has a slender cutting shank 20 and a base 18 with a threaded stud 19 for connection to a core assembly 21 contained within the casing (FIG. 6). When activated, core 21 ultrasonically vibrates tip 16 in an axial direction to emulsify the natural lens. Tip 16 has a central bore 22 coupled to a passage 23 in core 21. Passage 23 is, in turn, attached to a vacuum source (not shown) to aspirate the emulsified lens fragments from the eye.

Sleeve 10 includes a base 24, a cannula 26, and a transition segment 28 with a funnel-like configuration connecting the cannula and the base (FIGS. 1–6). The sleeve is preferably a unitary molded member composed of silicone. Nevertheless, the sleeve could be formed as an integrated assembly of multiple pieces, or formed of other pliable materials which are suitable for insertion into an eye during surgery.

Base 24 is a hollow segment that forms the proximal end of the sleeve (FIGS. 1–3 and 5–6). The interior surface 30 of base 24 is cylindrical to slide over the distal end 17 of casing 14. Alternatively, the base could be internally threaded for threaded attachment to the casing. Cannula 26 is a narrow, pliable tube which encircles the cutting shank 20 of tip 16 and defines an annular conduit 34 about tip 16 (FIGS. 1–6). Fluid is passed into passage 36 in casing 14 from a source (not shown), and directed to flow through conduit 34 and into the eye (FIG. 6). The fluid is provided to cool the instrument and irrigate the eye during the operation.

Figure 8:
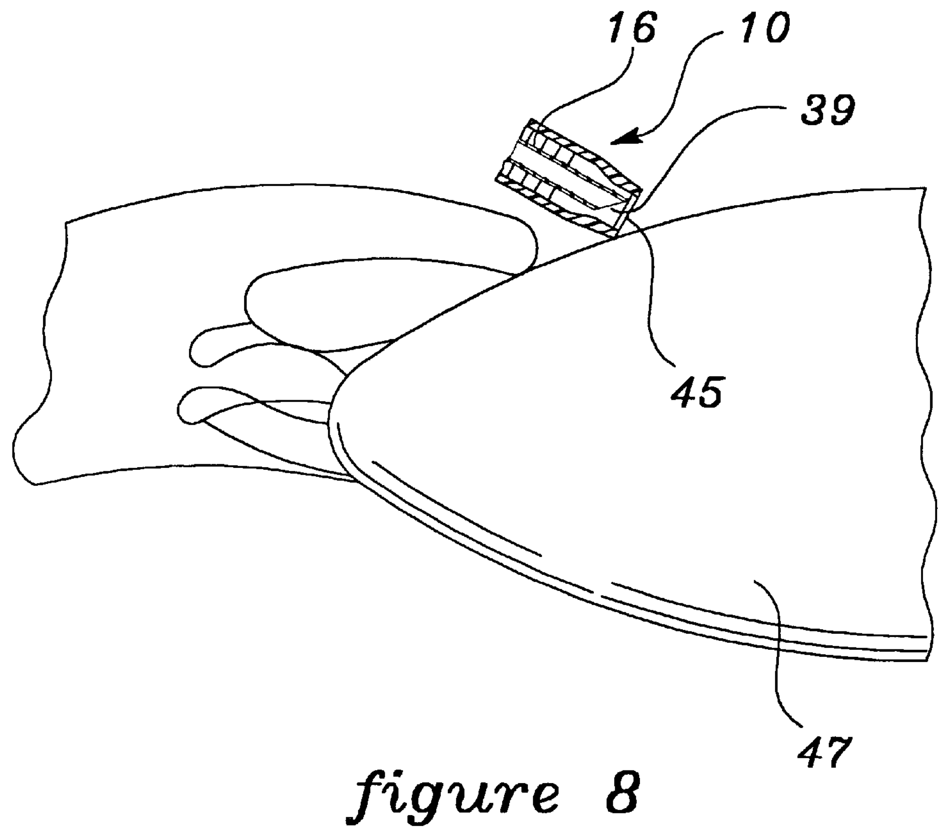
FIGS. 8 and 9 are partial, longitudinal cross-sectional views of the end of the instrument in use.

In an unstressed state, cannula 26 extends over the entire length of cutting tip 16 and beyond the free end 39 of the tip (FIGS. 6 and 8). In this way, sleeve 10 enshrouds tip 16 and thus protects the interior portions of the eye from being inadvertently injured by the exposed tip.

Cannula 26 preferably has a circular cross-sectional configuration, although other shapes may also be used. The interior wall 38 of cannula 26 is provided with a series of longitudinally spaced apart rings 40 (FIGS. 3–7). In the preferred construction, each ring 40 is formed by a pair of concave arcuate sidewalls 42 which taper inward to form a narrow inner edge 44. Opposing sidewalls 42 of adjacent rings 40 gradually merge to form generally U-shaped, annular channels 43 between the rings.

Figure 9:
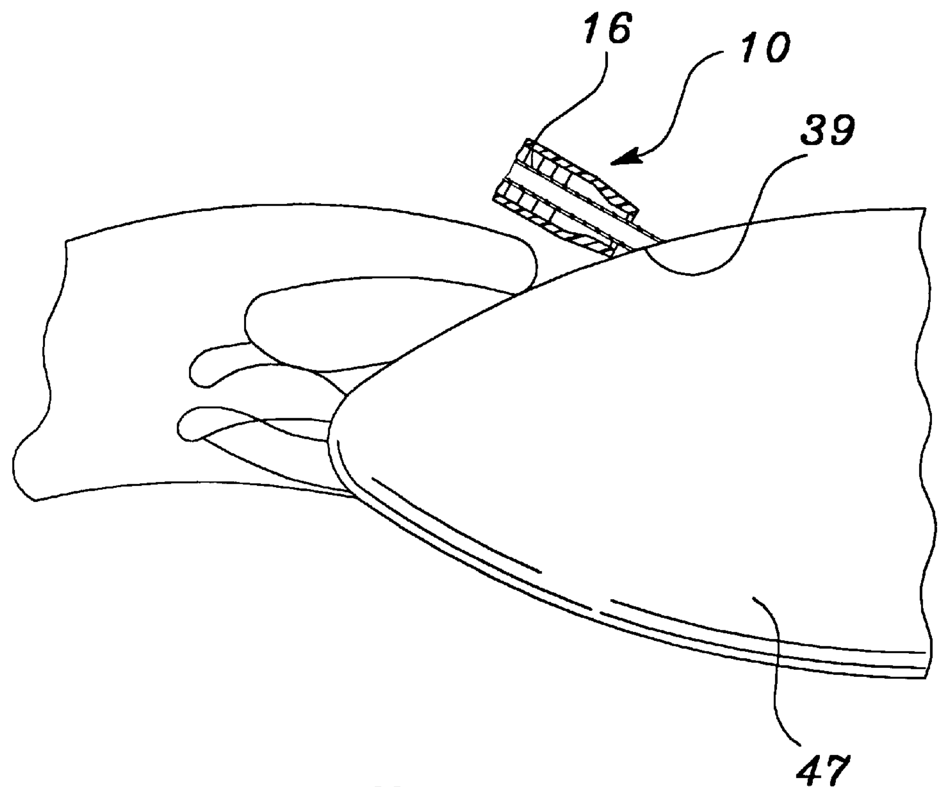

The formation of the rings on the thin wall of cannula 26 enables the cannula to be retracted rearwardly in order to expose the free end of tip 16 (FIGS. 7 and 9). More specifically, the surgeon abuts the free end 45 of cannula 26 against the natural lens 47 and presses surgical instrument 12 forward, to retract the cannula. This axial compressive force 48 applied by the surgeon causes the cannula to axially crumple or retract as a bellows or accordion. In particular, the portions of the cannula spanning between rings 40 will buckle outward such that the rings are axially moved closer together (FIG. 7). Further, the resilience of the sleeve material produces a forward biasing force which will automatically return cannula 26 to the extended position over tip 16 when instrument 12 is backed away from lens 47 (FIGS. 6 and 8).

In addition, rings 40 function to reduce the engagement between sleeve 10 and tip 16 to one or more line contacts when cannula 26 is laterally pressed against the corneal tissue.

In particular, when sleeve 10 and tip 16 are inserted through a small incision in the eye, cannula 26 is ordinarily snugly received into the incision such that corneal tissue engages the exterior surface 46 of the cannula. In an unstressed state, rings 40 are spaced from contact with cutting tip 16 to maximize fluid flow and minimize the generation of heat. Under these circumstances, the fluid passing through sleeve 10 flows primarily over rings 40 and axially along the exterior of the tip. As the surgeon manipulates the instrument, tip 16 at times laterally presses cannula 26 against the adjacent corneal tissue. In the present invention, rings 40 prevent the recessed channels 43 from engaging tip 16, and thus limits the contact between sleeve 10 and tip 16 to engagement with the narrow inner edges 44—which essentially form line contacts with the tip. The surface area contact between the sleeve and the cannula is thus kept very small when under lateral compression. Further, as mentioned above, the spaced apart rings 40 form annular channels 43 which extend around tip 16. When cannula 26 is pinched between the tip and the corneal tissue, channels 43 permit the fluid passing through sleeve 10 to circulate laterally about the entire tip even when compressed so that proper cooling can be maintained. As a result, the generation of heat due to the frictional contact of the vibrating tip against the sleeve is maintained within acceptable limits.

Figure 10:
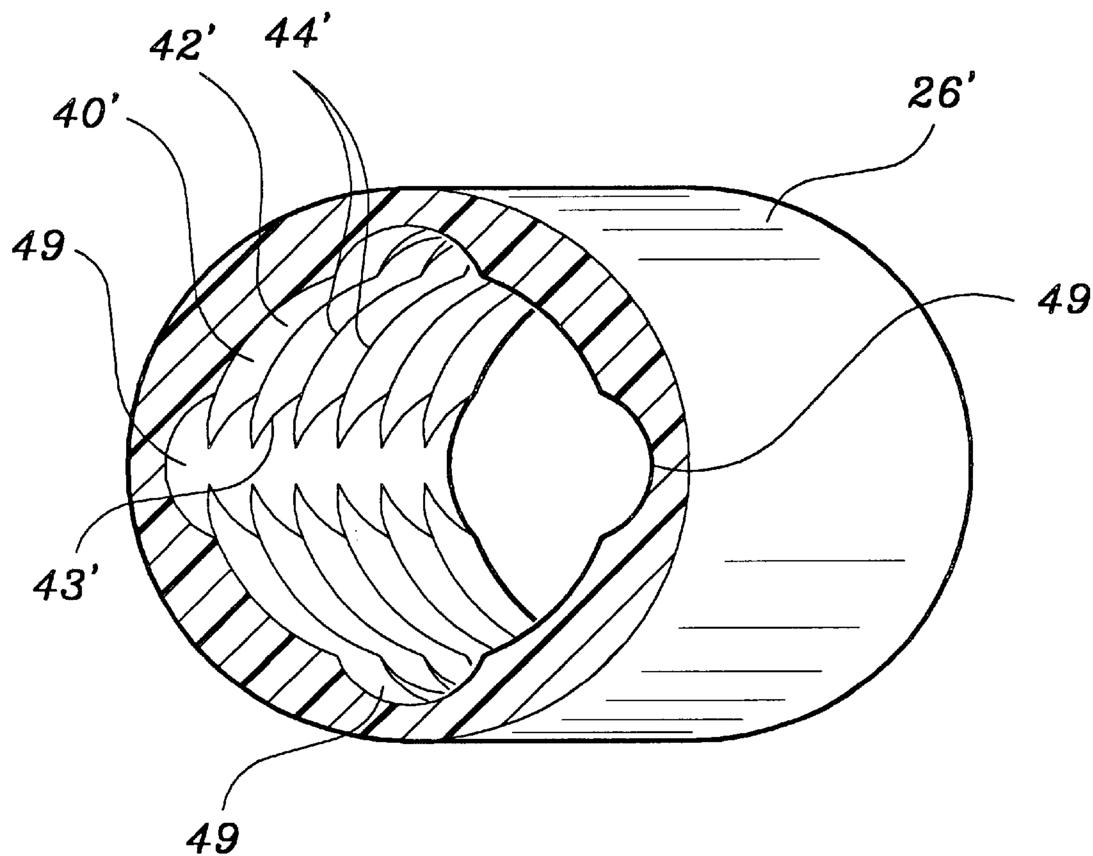
FIG. 10 is a partial perspective view of a cannula of a surgical sleeve of a second embodiment of the present invention.
Figure 11:
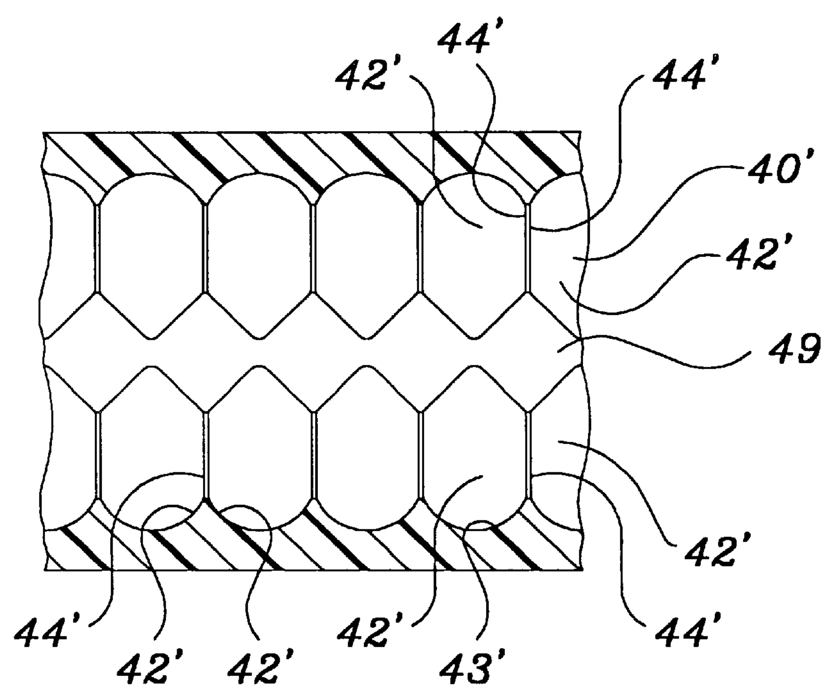
FIG. 11 is a longitudinal cross-section of a mid portion of the cannula of the second embodiment.

In one preferred construction, the rings project from wall surface 38 a distance of about 0.003 inches, and are spaced apart about 0.015 inches center to center (i.e., edge 44 to edge 44). Although the rings can extend continuously about the entire inner perimeter of cannula 26 (FIGS. 1–9), a plurality of spaced apart gaps 49 can alternatively be formed in rings 40' to permit enhanced longitudinal flow of the fluid in addition to lateral flow through channels 43' (FIGS. 10 and 11). In this alternative construction, rings 40' would include essentially the same construction of sidewalls 42' and inner edges 44' except for gaps 49. The gaps in the series of rings can be longitudinally aligned (FIGS. 10 and 11) or staggered relative to each other such that at least some of the gaps are angularly oriented relative to each other (not shown). The rings extend along substantially the entire length of the cannula (FIGS. 3 and 6); although the rings are only needed along the portions of the cannula expected to be positioned between the corneal tissue and the tip (i.e., in the region where the sleeve is likely to be pinched between the tip and the corneal tissue). Further, other arrangements, spacings, sizes and shapes of rings could be used to achieve the same objectives.

The above-discussion concerns the preferred embodiments of a sleeve adapted for attachment to a surgical instrument provided with a cutting tip that is driven to remove the natural lens of an eye. Variations in the drive and construction of the surgical instrument and in the sleeve construction may be made without departing from the spirit and broader aspects of the invention as defined in the claims.

We claim:

1. A surgical sleeve for use with an instrument to perform eye surgery, wherein the instrument includes a casing and a slender cutting tip projecting from the casing, said surgical sleeve comprising a tubular, pliable body having a base and a cannula, said base being attachable to the casing such that said cannula extends outward from said base and encircles the cutting tip to define a conduit between an interior surface of said cannula and the cutting tip for the passage of a fluid, said interior surface having a series of closely spaced rings along at least a portion of said cannula.

2. A surgical sleeve in accordance with claim 1 wherein each said ring extends inward from an interior surface of said cannula to minimize contact with the cutting tip when the cannula is under lateral compression.

3. A surgical sleeve in accordance with claim 2 wherein each said ring includes a pair of sidewalls which taper inwardly away from said interior surface of said cannula.

4. A surgical sleeve in accordance with claim 3 wherein each said sidewall has a generally concave configuration.

5. A surgical sleeve in accordance with claim 2 wherein each said ring is continuous about the entire interior perimeter of said cannula.

6. A surgical sleeve in accordance with claim 2 wherein at least one of said rings includes at least one gap for the passage of a fluid therethrough.

7. A surgical sleeve in accordance with claim 2 in which said rings on said interior surface of said cannula taper to form narrow peaks.

8. A surgical sleeve in accordance with claim 7 in which said peaks are separated by about 0.015 inches.

9. A surgical sleeve in accordance with claim 7 in which said interior surface between said peaks has a generally U-shaped configuration.

10. A surgical sleeve for use with a surgical instrument to perform eye surgery, wherein the instrument includes a casing and slender cutting tip projecting from the casing, said surgical sleeve comprising a tubular, pliable body having a base and a cannula, said base being attachable to the casing such that said cannula extends outward and enshrouds the entire length of the cutting tip when unstressed, said cannula including means to enable axial retraction of said cannula to expose the tip during use, wherein said cannula has an interior surface provided with a series of longitudinally spaced apart rings, and wherein at least one of said rings includes at least one gap for the passage of fluid therethrough.

11. A surgical sleeve in accordance with claim 7 wherein each said ring includes a pair of sidewalls which taper inwardly away from said interior surface of said cannula.

12. A surgical sleeve in accordance with claim 7 wherein each said sidewall has a generally concave configuration.

13. A surgical sleeve in accordance with claim 7 wherein each said ring is continuous about the entire interior perimeter of said cannula.

14. A surgical instrument for eye surgery comprising:

a casing;

a cutting tip projecting from the casing; and a surgical sleeve comprising a tubular, pliable body having a base and a cannula, said base being attached to the casing such that said cannula extends outward from said base and encircles the cutting tip to define a conduit between an interior surface of said cannula and the cutting tip for the passage of a fluid, said interior surface having a series of closely spaced rings along at least a portion of said cannula.

15. A surgical instrument in accordance with claim 14 wherein each said ring extends inward from an interior surface of said cannula to minimize contact with the cutting tip when the cannula is under lateral compression.

16. A surgical instrument in accordance with claim 15 wherein each said ring includes a pair of sidewalls which taper inwardly away from said interior surface of said cannula.

17. A surgical instrument in accordance with claim 16 wherein each said sidewall has a generally concave configuration.

18. A surgical instrument in accordance with claim 15 wherein each said ring is continuous about the entire interior perimeter of said cannula.

19. A surgical instrument in accordance with claim 15 wherein at least one of said rings includes at least one gap for the passage of a fluid therethrough.

20. A surgical instrument for eye surgery comprising:

a casing;

a cutting tip projecting from the casing; and a surgical sleeve comprising a tubular, pliable body having a base and a cannula, said base being attached to the casing such that said cannula extends outward and enshrouds the entire length of the cutting tip when unstressed, said cannula including means to enable axial retraction of said cannula to expose the cutting tip during use, wherein said cannula has an interior surface provided with a series of spaced apart rings, and wherein at least one of said rings includes at least one gap for the passage of a fluid therethrough.

21. A surgical sleeve in accordance with claim 19 wherein each said ring includes a pair of sidewalls which taper inwardly away from said interior surface of said cannula.

22. A surgical sleeve in accordance with claim 19 wherein each said sidewall has a generally concave configuration.

23. A surgical sleeve in accordance with claim 19 wherein each said ring is continuous about the entire interior perimeter of said cannula.

24. A process for surgically removing a natural lens from an eye comprising:

providing a surgical instrument including a casing, a slender cutting tip projecting from the casing and having a free end, and a pliable sleeve attached to said casing and having a cannula which enshrouds said entire cutting tip to cover said free end in an unstressed condition;

inserting said slender cutting tip and cannula through an incision in an eye;

pushing said cannula against the natural lens to apply an axial compressive force to the cannula to retract said cannula and expose the free end of the cutting tip;

driving said cutting tip to emulsify the natural lens; and aspirating the emulsified portions of the natural lens.

25. A process in accordance with claim 24 wherein the provided sleeve includes a series of spaced apart annular rings about an interior surface of the cannula.

26. A process in accordance with claim 24 wherein said aspirating step in accomplished by providing the cutting tip with a central bore and applying a vacuum pressure to the bore.

27. A process in accordance with claim 24 wherein said driving step includes subjecting the cutting tip to axial ultrasonic vibrations.

28. A process in accordance with claim 24 further including supplying a fluid between the cutting tip and the sleeve to cool the surgical instrument and irrigate the eye.

29. A surgical instrument for eye surgery comprising:

a casing;

a cutting tip projecting from the casing; and a surgical sleeve comprising a tubular, pliable body having a base and a cannula, said base being attached to the casing such that said cannula extends outward from said base and encircles the cutting tip to define a conduit about the cutting tip, said cannula having an interior surface provided with a plurality of spaced apart rings along at least a portion of said cannula, said rings being spaced from said cutting tip when said sleeve is in an unstressed condition.

30. A surgical instrument for eye surgery comprising:

a casing;

a cutting tip projecting from the casing and having an inner passage for aspirating material; and a surgical sleeve comprising a tubular, pliable body having a base and a cannula, said base being attached to the casing such that said cannula extends outward from said base and encircles the cutting tip to define a conduit between an interior surface of said cannula and the cutting tip for the passage of a fluid therethrough, said cannula including an interior surface and a series of spaced apart rings along at least a portion of said cannula.

* * * * *